United States Patent [19]
Groux

[11] Patent Number: 5,800,477
[45] Date of Patent: Sep. 1, 1998

[54] HAIR GROWTH METHOD AND APPARATUS

[75] Inventor: Paul D. Groux, Vallejo, Calif.

[73] Assignee: Allied Health Association, Inc., Englewood, Colo.

[21] Appl. No.: 802,485

[22] Filed: Feb. 20, 1997

[51] Int. Cl.⁶ ................................................ A61N 1/32
[52] U.S. Cl. .................................................. 607/76
[58] Field of Search ............... 607/2, 3, 50, 76, 607/139, 145, 150, 153; 601/12, 15, 133

[56] References Cited

U.S. PATENT DOCUMENTS

| | | | |
|---|---|---|---|
| 682,089 | 9/1901 | Leach | 607/153 |
| 861,349 | 7/1907 | Beaubien | |
| 1,534,444 | 4/1925 | Feldheym | |
| 1,811,764 | 6/1931 | Sherwood | |
| 1,948,067 | 2/1934 | De Carreno et al. | |
| 2,480,029 | 8/1949 | Jozsy | |
| 2,959,167 | 11/1960 | Leclabart | |
| 3,872,859 | 3/1975 | Pitzen et al. | |
| 4,175,551 | 11/1979 | D'Haenens et al. | |
| 5,251,623 | 10/1993 | Groux et al. | 607/50 |
| 5,484,387 | 1/1996 | Pitzen | |

FOREIGN PATENT DOCUMENTS

| | | |
|---|---|---|
| 2 484 262 | 3/1980 | France |
| 2040 181 | 8/1970 | Germany |
| 150643 | 9/1920 | United Kingdom |

Primary Examiner—William E. Kamm
Attorney, Agent, or Firm—Brian D. Smith, P.C.

[57] ABSTRACT

Method and apparatus for growing hair on a subject's scalp are disclosed. The method includes pinching an area of a subject's scalp having hair bulbs for at least 2 seconds with a pair of electrodes. The electrodes are energized so that they pass a low voltage, low current and low frequency signal through the pinched area of the subject's scalp. The frequency of the signal is preferably less than about 6 Hz and the current thereof is preferably between about 50 and 800 microamps. The foregoing process is periodically repeated over several weeks, preferably months, to regrow or enhance the growth of hair on the treated area. The frequency and current of the signal are also preferably altered or varied each treatment for optimum results.

27 Claims, 4 Drawing Sheets

HAIR GROWTH METHOD AND APPARATUS

TECHNICAL FIELD OF THE INVENTION

The invention relates generally to method and apparatus for promoting the growth and the regrowth of hair in humans.

BACKGROUND OF THE INVENTION

Many individuals are troubled by premature baldness, receding hairlines, or other conditions in which hair is lost from the head. Over the years, a variety of chemicals have been marketed as hair regrowth aids but with mixed, generally disappointing results. Many individuals have invested considerable sums in artificial hair pieces. Some individuals have even undergone surgical hair implantation procedures requiring the exercise of highly skilled medical expertise which is generally unavailable to a wide cross-section of potential beneficiaries. It will thus be appreciated that there is a need for a reasonably inexpensive hair regrowth process capable of being administered by relatively unskilled personnel and capable of promoting hair regrowth in the widest possible population cross-section.

The prior art discloses that a variety of electrical stimuli have been employed in an effort to promote hair growth. For example, U.S. Pat. No. 861,349 issued Jul. 30, 1907 for an invention of R. E. Beaubien entitled "Apparatus for Treating the Scalp" discloses an "apparatus for promoting the growth of hair upon the human head." The apparatus appears to rely upon a combination of pneumatic, vacuum and electrical effects, in combination with the application of medicated lotions and massage to the scalp. According to Beaubien, any desirable form of electrical battery or current may be used. The present applicant however believes that this is not the case and that in order to satisfactorily promote hair regrowth, specific electrical signals must be employed.

U.S. Pat. No. 735,581 issued Aug. 4, 1903 for an invention of Pollacsek, et al. entitled "Therapeutical Apparatus" discloses a device "by means of which vibrations of diseased parts of the body can be produced." Pollacsek, et al. indicate that the device may be shaped as a cap to be placed on the head and that the cap may be introduced into a magnetic field produced by an electric current passing through the windings of an iron core. However, there is no indication of the specific nature of the electric or magnetic signals or fields employed, nor is there any suggestion that Pollacsek, et al. considered applying their device to promote hair regrowth.

U.S. Pat. No. 740-385 issued Oct. 6, 1903 for an invention of W. B. Bassell entitled "Electrotherapeutic appliance" provides another device "adopted to subject the wearer to the action of a current of electricity for curative purposes". Bassell explains that his invention is to be utilized for the relief and cure of nervousness, insomnia, headache, and other kindred troubles. He suggests that this may be accomplished by subjecting the head and the wearer to the action of a comparatively mild current of electricity provided by a small battery. Again however there is no suggestion that Bassell considered the use of his device to promote hair regrowth, nor are any specific electrical signals discussed.

U.S. Pat. No. 3,872,859 issued Mar. 25, 1979 for an invention of Pitzen, et al. entitled "Method and Device for Stimulating the Organs Associated with the Human Scalp" examines the problem of promoting hair growth in some detail. Pitzen, et al. provide a method and apparatus in which a plurality of wave form generators output signals having frequencies varying from 230 hertz through 2650 hertz. The waveform generators are also pulsed at repetition rates varying from 3 times per second to 26 times per second. The signals so produced are applied to hand-held massaging electrodes which are in turn applied to the subject's scalp.

Published French patent application No. 2,484,262 of Paul Maurice Viallis provides another electrical apparatus and method for treating the human scalp to combat seborrhoea, hair loss, dandruff, etc. A conductive electrode cap is fitted over the scalp and a secondary electrode is placed in contact with another area of the body. A current of the order of 8–15 mA is applied for a period of 5 to 30 minutes depending upon the type of complaint and type of treatment prescribed. The object of Viallis' invention is apparently to ionize the scalp area so that ointments or other applied treatment compositions may penetrate the scalp with greater effectiveness.

Published West German patent application No. 3,618,933 discloses an invention of Masaki, et al. pertaining to an electrotherapeutic device for promoting eyebrow hair growth. The apparatus is shaped to fit on a patient's head. Electrodes are applied to the eyebrows. A pulse-like current preferably having a square or trapezoid waveform is applied to the electrodes, with a biphasic action, potential-like oscillation having a frequency in the $1/500$ to $1/200$ second range and pulsed at a frequency of 0.5 to 2 seconds is preferably applied to the electrodes.

Two published British patent application Nos. 21,60,426A and 2,160,427A of Masaki appear to correspond to the West German application aforesaid, although the British applications do not appear to restrict themselves to eyebrow hair growth.

My own previous work embodied in U.S. Pat. Nos. 5,251,623 and 5,336,247 is directed to a method and apparatus for enhancing the regrowth of hair. The method includes one or more electrodes which are positioned closely proximate the subject's scalp. A low voltage electrical signal having a frequency of about 7.86 hertz or about 15.72 hertz is continuously applied to the electrodes for about 12 minutes. The polarity of the signal may be either positive or negative. A complete hair regrowth treatment cycle typically spans about 32 weeks, during which time the subject undergoes a sequence of two 12 minute treatments per week as aforesaid. The frequency, signal polarity, and voltage level are preferably varied each treatment according to a schedule which is described in my patents.

The hair growth apparatus disclosed in my previous patents comprises at least one electrode adapted to be positioned closely proximate the subject's scalp, a voltage pulse generator means electrically coupled to the electrode (s) for application thereto of a low voltage pulse train, and a frequency selector means electrically coupled to the voltage pulse generator means for varying the frequency of the pulse train. The apparatus also includes preferably signal polarity selector means electrically coupled between the voltage pulse generator means and the electrode(s), for varying the polarity of the pulse train. The electrodes are advantageously mounted within a hood positionable over the subject's head.

DISCLOSURE OF THE INVENTION

My present invention is directed to another hair growth method (and apparatus for carrying out the method) which involves direct electrode contact with the subject's skin and the use of extremely low frequency electrical signals. Specifically, the method includes positioning a pair of electrodes in spaced relationship on an area of a subject's skin having hair bulbs, preferably the subject's scalp. A low voltage, low current signal is passed between the positioned electrodes for at least two seconds with the signal preferably having a frequency of less than about 6 hertz. The foregoing process is periodically repeated over several weeks to regrow or enhance the growth of hair on the treated area.

In a preferred embodiment, a small targeted area of the subject's scalp possessing only a small number of hair bulbs is pinched with a pair of wetted, cotton swab-type electrodes for about 4 seconds as the aforementioned signal is applied. A single treatment would typically include treating a plurality of adjacent small areas on a subject's scalp until all areas requiring hair regrowth are treated. The treatment is preferably repeated at least twice a week over at least a three week period for preferred results. In a particularly preferred embodiment, the frequency of the applied signal is between about 0.6 and 1.2 hertz, the voltage of the signal is preferably less than about 9 volts, preferably between 0.5 and 8 volts, and the current of the signal is preferably between about 50 and 800 microamps. The frequency and current of the signal are also preferably altered or varied each treatment for optimum results, i.e. hair regrowth.

BRIEF DESCRIPTION OF THE DRAWINGS

The invention will be more readily understood by reference to the accompanying drawings wherein like reference numerals indicate like elements throughout the drawing figures, and in which.

DETAILED DESCRIPTION OF A PREFERRED EMBODIMENT

Figure 1:
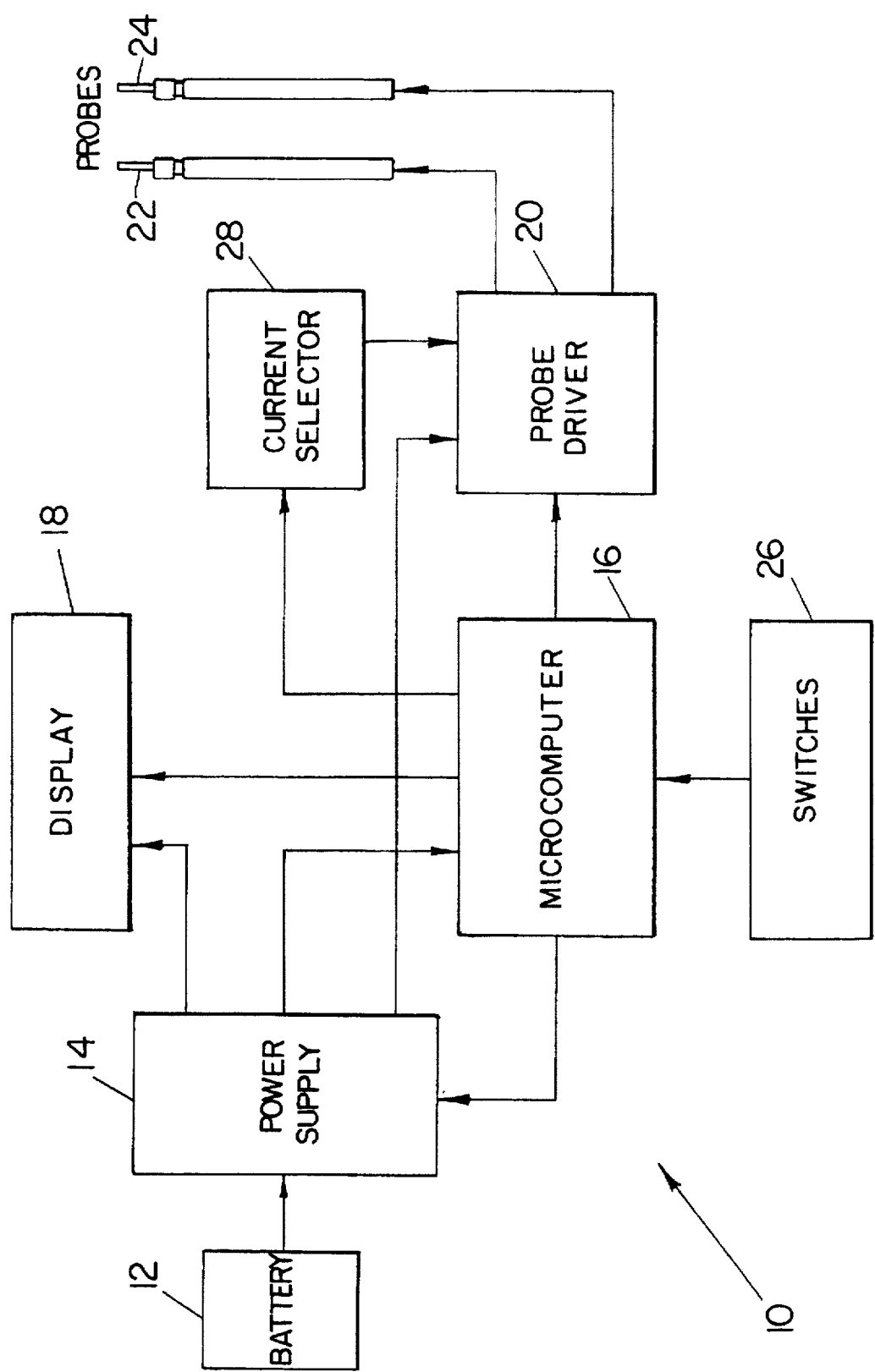
FIG. 1 is a block diagram of a hair growth apparatus constructed in accordance with a preferred embodiment of the invention.

As indicated in FIG. 1, the system which is referred to generally as portable unit 10 is powered by a 9 volt battery 12. Battery 12 is connected to a power supply circuit 14 which supplies power to the unit's microcomputer circuit 16, display circuit 18 as well as the unit's probe driver circuit 20 which is connected to probes 22, 24, as such is described in more detail below with respect to FIGS. 2, 2a.

Push-button switches (identified generally by numeral 26 in FIG. 1) connected to microcomputer 16 enable one to turn the microcomputer on or off by putting the microcomputer in an awake or sleep state. In the awake state, a clock signal from microcomputer 16 is supplied to power supply 12 to activate a voltage doubler circuit (described below) which supplies power to probe driver circuit 20. Other push-buttons of switches 26 as shown in more detail in FIG. 3 allow the operator to select the current (i.e. intensity) and one of two pre-set signal frequencies of the signal supplied to the probes. One set of outputs from the microcomputer is connected a current selector 28 which sets the operating current of the probe driver. Another set of the outputs is connected to the display circuit 18 which displays the settings.

The final set of outputs is connected directly to the probe driver which sets the polarity of the probe signal. The instructions in the microcomputer cause the output current of probe driver 20 to be switched in a manner which sets the polarity and frequency of the probe output, as more fully described below.

The apparatus of the preferred embodiment will now be described in greater detail with reference to the electronic circuit diagram of FIG. 2.

Power for microcomputer 16 and display circuit 18 of unit 10 is supplied by 9 volt battery B1 which is reduced to 5 volts by a low power, low dropout, regulator U2. Power for probe driver circuit 20 (also supplied by battery 10) has its voltage increased by a voltage doubler circuit. It is necessary to increase the voltage to the probe driver circuit to compensate for the loss of voltage which occurs as the battery ages.

The voltage doubler comprises D2, D3, C2, C3, R1–R4 and Q1–Q3. When microcomputer 16 (identified in FIG. 2 as U4) is operating, it's oscillator (which includes crystal X1 and capacitors C6 and C7) supplies a signal to the base of transistor Q1. Transistor Q1 inverts the signal and supplies it to switching transistors Q2 and Q3. When Q2 is conducting, capacitor C2 is charged through diode D2. Transistor Q3 then conducts and dumps the charge on C2 through D3 to capacitor C3. With successive cycles capacitor C3 charges to approximately twice the battery voltage. Note that this circuit is shut down when the unit is off, or in sleep mode, thus conserving battery power. The doubled voltage is then supplied to an adjustable voltage regulator U2. The output voltage of U2 is set to a value of about 11 volts by the ratio of resistors R6 and R7 which limits the voltage to the operational amplifiers which have a rated maximum voltage of 12 volts. Capacitors C1 and C4 reduce noise and prevent oscillation in the voltage regulators. Diode D1 prevents damage from reverse polarity of battery B1 caused by improper battery installation.

Probe driver 20 consists of operational amplifiers U3A and U3B as well as resistors R17–R26. The amplifiers are low power, "rail-to-rail" type amplifiers and are identically configured as modified "Howland" circuits to provide constant current to the probe. Current selector 28 as identified in FIG. 1 consists of resistors R8–R13 and R16.

In conjunction with operational amplifier U3A, resistors R17, R18, R21, R22 and R25 are proportioned to provide an output of 500 microamperes per volt of input on resistor R18. Resistors R8 through R13 and R16 along with the loading caused by resistors R18 and R20 form a programmed precision voltage source for the two circuits. The left ends of resistors R8 through R13 connect to outputs from one register of the microcomputer. These points in the circuit are normally held at ground potential by the microcomputer and are raised to a 5 volt level to select the output current. For example, raising the register output to R8 provides a voltage of 1.6 volts to the junction of resistors R8 through R13, R16, R18 and R20 thus programming the probe output to be 800 microamperes. Only one line is raised at any time.

Probe 22 is connected to the junction of resistors R22 and R25. The second probe 24 is connected to the junction of resistors R24 and R26. When the programmed voltage is being supplied to both operational amplifiers, the differential voltage across the probes would be zero and no current would pass through a skin load.

To pass current from one probe to the other through a skin load, one of transistors Q4 and Q5 is used to clamp its circuit to ground potential so that its probe receives the current provided by the other circuit. These transistors are connected to the microcomputer register through resistors R14 and R15 so that the output polarity can also be selected by the microprocessor by raising one line at a time. Since the hair growth method of the present invention requires the ability to produce a maximum output of 800 microamperes into a skin resistance loading of 10,000 ohms, this dictates that a minimum of 8 volts be supplied to the probe.

Figure 3:
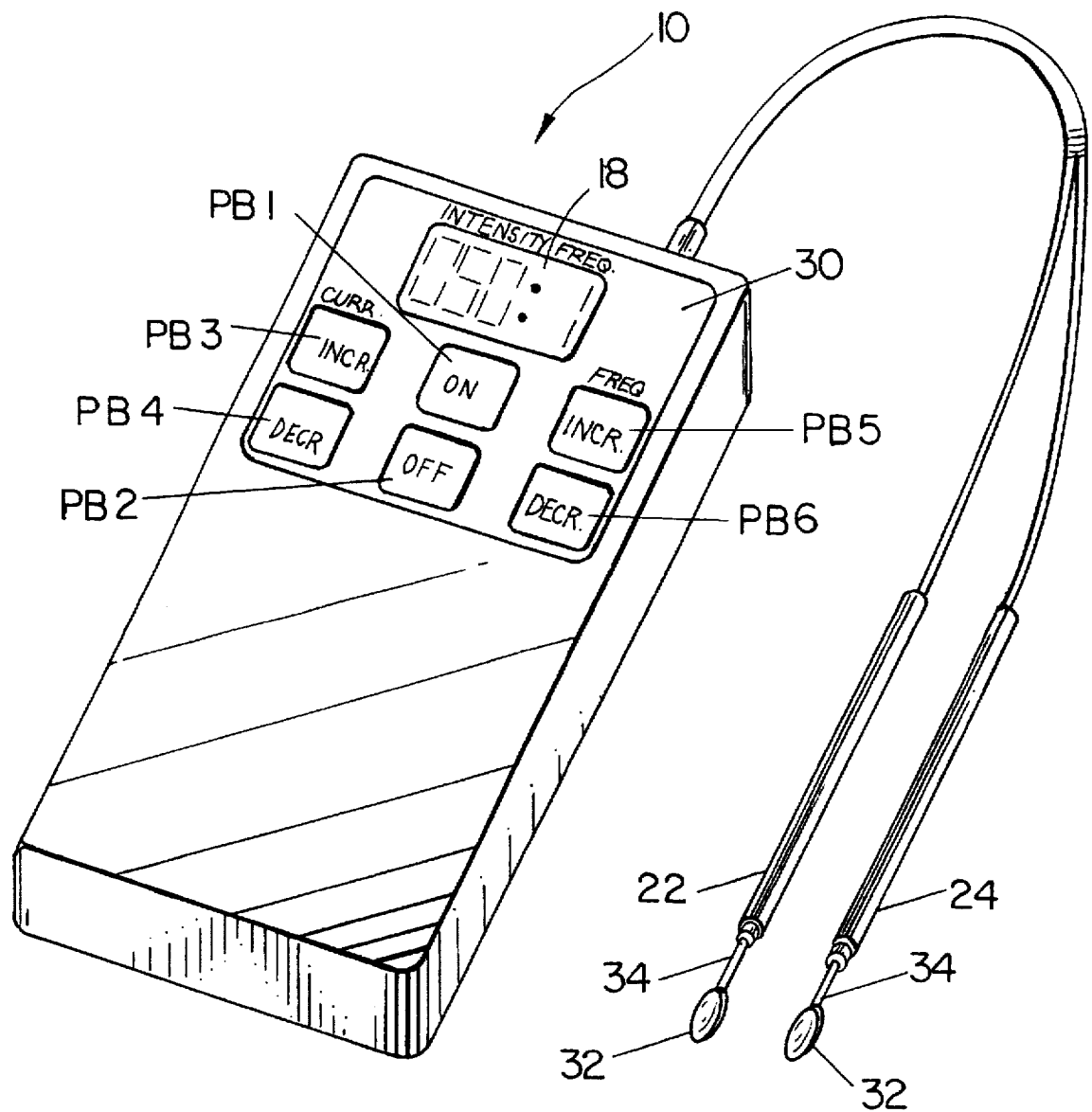
FIG. 3 is a perspective view of the apparatus of FIG. 1.

Referring now to FIG. 3, it will be appreciated that switches 26 of FIG. 1 are individually identified in FIG. 3 as push button switches PB1 through PB6 and as illustrated therein are located on a keypad 30 of portable unit 10. The microcomputer is normally in a "sleep" state meaning that its oscillator has been stopped. The microcomputer is awakened by pressing push-button PB1. This supplies a low input to the microcomputer causing it to reset and restart the oscillator. A preferred microcomputer for use as microcomputer 16 in accordance with the present invention is manufactured by Microchip Technologies of Chandler, Arizona, Model No. PIC16C55. Upon starting, the microcomputer will initialize and wait for further input from one of the push-buttons. Push-button PB2 is programmed to stop the microcomputer by putting it into a sleep state. Push-button PB3 is programmed to increase the output current with each successive button press and push-button PB4 is programmed to decrease the output current with each successive button press. Push-button PB5 is programmed to select the higher preset output frequency which as described below is preferably 1.2 Hz. Push-button PB6 is programmed to select the lower preset output frequency which as described below is preferably 0.6 Hz. The selected output current and frequency are displayed on display 18 which is preferably a four digit LED, i.e. light emitting diode, display wherein each digit display is comprised of a multiplexed seven segment LED.

Returning to FIG. 2, the LED segments are connected directly to the outputs of register B in the microcomputer while the common terminals are driven by transistors Q6 through Q9 which are driven by microcomputer register A. The microcomputer's B register connections RB0 through RB5 are also used to read out the push-button switches. This is done by successively lowering the RB0 and RB1 terminals and reading the input on the RB2 through RB5 leads. The register C connections RC0 through RC7 are used to program the probe current and polarity as discussed in the description on the probe driver circuit above.

Figure 2:
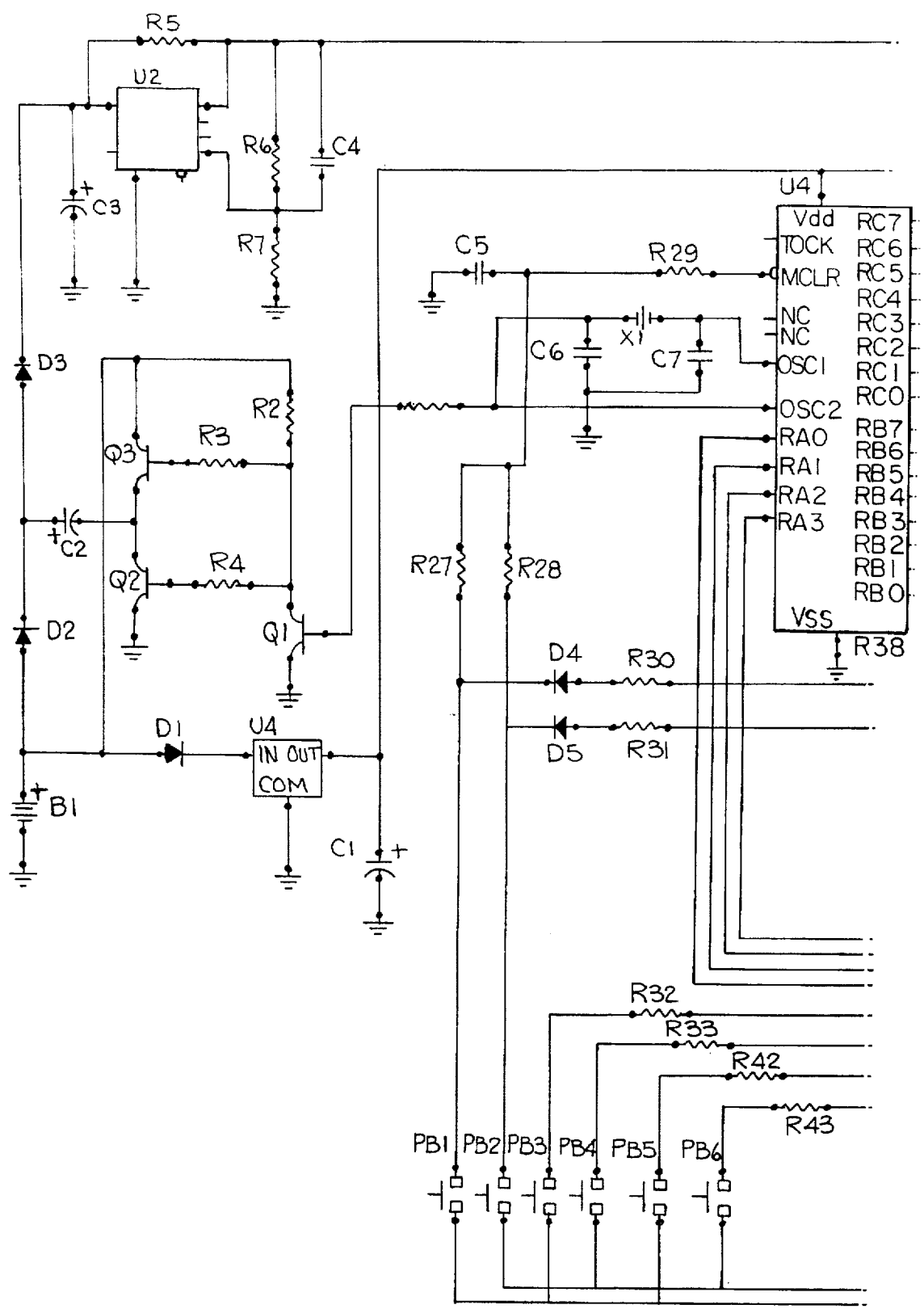
FIG. 2 is a portion of an electronic circuit schematic diagram of the apparatus of FIG. 1.
Figure 2A:
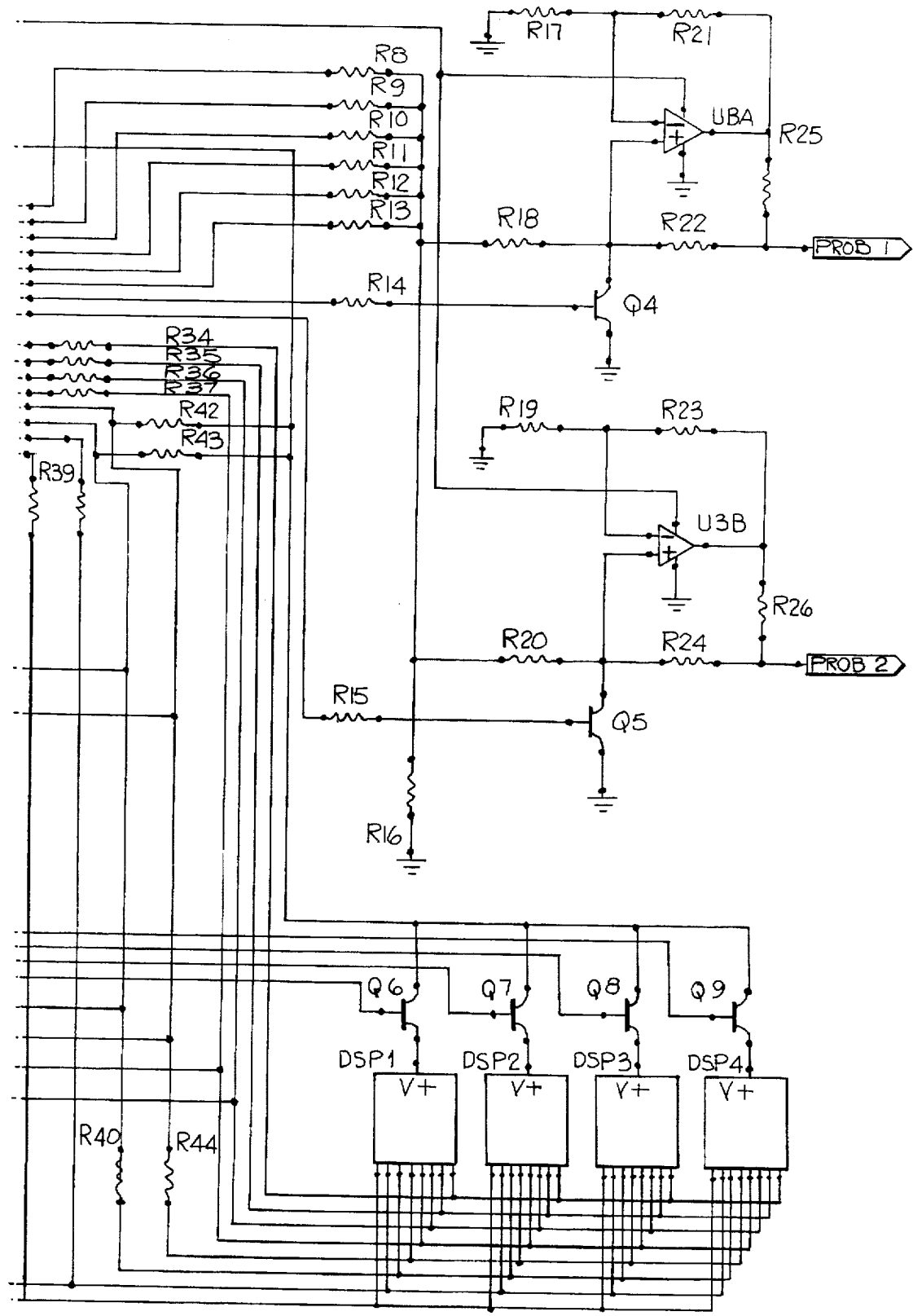
FIG. 2A is the remaining portion of the electronic circuit schematic diagram of FIG. 2.

Parts used in the microcomputer circuit 16 of unit 10 as identified in FIG. 2 are as follows: D4 and D5 are 1N4148 diodes, Q6–Q9 are 2N3904 NPN transistors, C6 and C7 are 56 pF capacitors, U4 is the previously identified Microchip PIC16C55 Microcomputer, X1 is a 32,768 Hz Crystal, C-Type, Epson # C-001R 32.768K-A manufactured by Epson of Japan, C5 is a 0.1 uF capacitor, R30–R33 are 10 k$\Omega$, 10% resistors, R34–R41 are 220$\Omega$, 10% resistors, SIP, R42 and R43 are 100 k$\Omega$, 10% resistors, R27, R28 are 4.7 k$\Omega$, 10% resistors and R29 is a 100 $\Omega$, 10% resistor.

Parts used in the probe driver circuit 20 of unit 10 as identified in FIG. 2 are as follows: Q4 and Q5 are 2N3904 NPN transistors, U3A and U3B are Motorola MC33202 Operational Amplifiers manufactured by Motorola Inc. of Phoenix, Ariz. R21–R24 are 165 k$\Omega$, 1% resistors, R17–R20 are 330 k$\Omega$, 1% resistors, R25 and R26 are 1 k$\Omega$, 1% resistors, R10 is a 17.4 k$\Omega$, 1% resistor, R11 is a 8.66 k$\Omega$, 1% resistor, R12 is a 5.62 k$\Omega$, 1% resistor, R13 is a 4.32 k$\Omega$, 1% resistor, R9 is a 34.8 k$\Omega$, 1% resistor, R8 is a 69.8 k$\Omega$, 1% resistor, R16 is a 10.7 k$\Omega$, 1% resistor and R14 and R15 are 10 k, 10% resistors.

Parts used in the power supply driver circuit 14 of unit 10 as identified in FIG. 2 are as follows: Q1 and Q2 are 2N3904 NPN transistors, C1 and C2 are 1 uF capacitors, C3 is a 0.5 uF capacitor, D1–D3 are 1N4148 diodes, Q3 is a 2N3905 transistor, PNP, 9V Battery, End terminal type, U1 is a Motorola LP2950CP-5 Voltage Regulator, Low Power, Low Dropout, U2 is a Motorola LP2951CP-5 Adjustable Voltage Regulator, Low Power, Low Dropout, C4 is a 0.01 uF capacitor, R1 is a 47 k$\Omega$, 10% resistor, R3 and R4 are 18 k$\Omega$, 10% resistors, R2 is a 4.7 k$\Omega$, 10% resistor, R6 is a 787 k$\Omega$, 1% resistor and R5 and R7 are 100 k$\Omega$, 1% resistors.

OPERATION

To use portable unit 10 in accordance with the present invention for enhancing the growth or regrowth of hair, one first turns the unit on as previously mentioned by pressing the PB1 button on key pad 30 of the unit. One then sets the frequency and current of the signal to be applied to a subject's scalp by pushing the appropriate buttons provided therefore, i.e. buttons PB3 or PB4 for respectively increasing or decreasing the current, and buttons PB5 or PB6 for selecting the preset high or preset low frequency which are preferably preset at 0.6 and 1.2 Hz as previously described.

As shown in FIG. 3, a current of 50 microamps has been selected and in accordance with the hair growth method of the present invention, unit 10 has the capability of providing any current from 50 to 800 microamps. The numeral 1 illustrated in FIG. 3 with respect to the frequency indicates that the lower preset frequency has been selected, i.e. 0.6 Hz. The display of numeral 2 would indicate the selection of the higher preset frequency, i.e. 1.2 Hz.

Prior to using unit 10 on the subject's scalp, a cotton swab 32 preferably a Q-tip type swab is inserted into the tip 34 of each probe 22, 24. The cotton swabs 32 are then dipped into a saline solution which because of its salt content facilitates a good electrical connection between each probe and the subject's scalp to which the probe is to be applied.

The probes are now ready to be applied to the subject's scalp and are grasped by the individual who is to perform the treatment so that the individual has one probe in each hand. It will be appreciated from the following description that the treatment is so simple that it may be carried out by the subject himself. That is, the subject should be able to grasp a probe with each hand and perform the following procedure with little or no difficulty.

In any event, with a probe in each hand, the individual performing the treatment pinches or massages a small area of the subject's scalp with the probes. A small area as used herein means an area of the subject's scalp that may only possess a small number of hair bulbs, and which may have a diameter of a half an inch or less. Pinching as used herein means literally pinching or grabbing a small area of the subject's scalp with the probes so that the small area of the scalp is actually located or positioned between the cotton swab ends 32 of probes 22, 24.

The pinching process only needs to be performed on a targeted area for a short period of time, about four seconds. In fact, two seconds may be sufficient as long as the aforementioned signal having the desired current and frequency is applied to the area as it is pinched.

At the end of this pinching period, one then immediately repeats the pinching process on an adjacent area of the subject's scalp requiring treatment, again preferably for about a four second period. This process is repeated until all areas of the scalp requiring hair regrowth are treated. As will be appreciated, depending on the size of area of the scalp requiring treatment, the process should not take more than five or ten minutes to complete on most individuals.

The foregoing treatment is preferably repeated at least twice a week over a three week period or until a desired amount of hair is grown. The frequency and current of the signal are also preferably varied each treatment within a range of currents and frequencies believed to provide good results. Frequencies which have been found to provide particularly good results are 0.6 Hz and 1.2 Hz which are the frequencies programmed into unit 10. However, it is believed that any frequency below 6 Hz will provide good results and hair regrowth on some individuals may be possible with frequencies as high as 15 Hz and perhaps as high as 80 Hz. It has also been found that the current of the signal should be between 50 and 800 microamps. In addition, the voltage of the signal should be preferably less than about 9 volts with optimum results obtainable between about 0.5 and 8 volts. It may also be desirable to change the polarity of the signal or a bipolar signal may be used as provided by the electronics of unit 10.

It also needs to be mentioned hat while it is preferable to pinch the subject's scalp as described above, hair growth is possible in accordance with the present invention by merely massaging the scalp with the energized electrodes or probes. In fact, the mere stationary (but spaced) placement of the energized probes on a small area of the subject's scalp should promote hair growth. However, the results obtained with stationary placement are not expected to be as good as those obtainable by pinching as described above.

This invention has been described in detail with reference to a particular embodiment thereof, but it will be understood that various other modifications can be effected within the spirit and scope of this invention.

What is claimed is:

1. A hair growth method comprising the steps of:
    energizing a pair of electrodes with an electrical signal which is sufficient to facilitate the growth of hair from hair bulbs on a subject's scalp;
    pinching a first area of a subject's scalp having hair bulbs with said energized pair of electrodes for at least 2 seconds; and,
    periodically repeating the foregoing steps to facilitate the growth of hair from the hair bulbs on the first area of the subject's scalp.

2. A hair growth method as claimed in claim 1 further comprising pinching a second area of a subject's scalp having hair bulbs with said energized pair of electrodes for at least 2 seconds.

3. A hair growth method as claimed in claim 2 wherein the first area is adjacent the second area.

4. A hair growth method as claimed in claim 1 wherein said step of pinching is carried out for about 4 seconds.

5. A hair growth method comprising the steps of:
    energizing a pair of electrodes with a low current, low voltage, low frequency signal;
    pinching a plurality of adjacent areas on a subject's scalp with said energized pair of electrodes for at least 2 seconds per area; and,
    repeating the foregoing steps at least twice per week to regrow or enhance the growth of hair on the plurality of adjacent areas of the subject's scalp.

6. A hair growth method as claimed in claim 5 wherein the frequency of the signal is less than about 15 Hz.

7. A hair growth method as claimed in claim 5 wherein the frequency of the signal is below about 6 Hz.

8. A hair growth method as claimed in claim 5 wherein the frequency of the signal is between about 0.6 and 1.2 Hz.

9. A hair growth method as claimed in claim 5 wherein the voltage of the signal is less than about 9 volts.

10. A hair growth method as claimed in claim 5 wherein the voltage of the signal is between about 0.5 and 8 volts.

11. A hair growth method as claimed in claim 5 wherein the signal is a square wave.

12. A hair growth method as claimed in claim 5 wherein the steps are repeated at least twice a week for six weeks.

13. A hair growth method as claimed in claim 5 wherein the steps are repeated at every other day for three weeks.

14. A hair growth method as claimed in claim 5 wherein the signal is bipolar.

15. A hair growth method as claimed in claim 5 wherein the frequency of the signal is periodically altered.

16. A hair growth method as claimed in claim 5 wherein the voltage of the signal is periodically altered.

17. A hair growth method as claimed in claim 5 wherein the polarity of the signal is periodically altered.

18. A hair growth method as claimed in claim 5 wherein the current of the signal is between about 50 and 800 microamps.

19. A hair growth method as claimed in claim 5 wherein the electrodes are of the cotton swab type.

20. A hair growth method as claimed in claim 5 further comprising dipping each cotton swab electrode in saline solution.

21. A hair growth method as claimed in claim 5 wherein said step of pinching is carried out for about 4 seconds.

22. A hair growth method comprising the steps of:
    positioning a pair of electrodes in spaced relationship against a first area of a subject's skin having hair bulbs;
    passing low voltage current between the positioned electrodes wherein the current has a frequency of less than about 6 Hz; and,
    periodically repeating the foregoing steps to regrow or enhance the growth of hair on the first area of the subject's skin.

23. A hair growth method as claimed in claim 22 further comprising pinching the first area of the subject's skin with the electrodes for at least two seconds.

24. A hair growth apparatus comprising:
    a pair of hand held devices, each of which has a cotton swab type electrode;
    hand held, battery operated means for energizing said electrodes so that they are capable of passing a signal having a selected frequency between about 0.4 and 6.0 Hz, a selected current between about 50 and 800 microamps and a voltage between about 0.5 and 9.0 volts when said electrodes are proximate each other and in contact with a subject's scalp; and,
    means for selecting the signal's frequency and current.

25. A hair growth apparatus as recited in claim 24 further comprising means for displaying the selected frequency and current.

26. A hair growth apparatus as recited in claim 25 wherein said display means includes a member selected from the group consisting of light emmiting diodes and liquid crystals.

27. A hair growth apparatus as recited in claim 24 wherein said means for selecting the frequency and current includes push buttons.

* * * * *